(12) United States Patent
McNicholas

(10) Patent No.: US 6,972,033 B2
(45) Date of Patent: Dec. 6, 2005

(54) ACCOMMODATING INTRAOCULAR LENS ASSEMBLY WITH MULTI-FUNCTIONAL CAPSULAR BAG RING

(75) Inventor: Thomas McNicholas, LaGuna Niguel, CA (US)

(73) Assignee: Advanced Medical Optics, Inc., Santa Ana (*) Notice: Subject to any disclaimer, the term of this patent is extended or adjusted under 35 U.S.C. 154(b) by 36 days.

(21) Appl. No.: 10/227,927

(22) Filed: Aug. 26, 2002

(65) Prior Publication Data
US 2004/0039446 A1 Feb. 26, 2004

(51) Int. Cl.[7] .............................................. A61F 2/16
(52) U.S. Cl. .................................... 623/6.37; 623/6.41
(58) Field of Search ............................... 623/6.11, 6.16, 623/6.22, 6.37, 6.39–6.45, 6.49, 6.52–6.54, 623/6.38

(56) References Cited

U.S. PATENT DOCUMENTS

| | | | |
|---|---|---|---|
| 1,483,509 A | 2/1924 | Bugbee | |
| 2,129,305 A | 9/1938 | Feinbloom | |
| 2,274,142 A | 2/1942 | Houchin | |
| 2,405,989 A | 6/1946 | Beach | |
| 2,511,517 A | 6/1950 | Spiegel | |
| 3,031,927 A | 5/1962 | Wesley | |
| 3,034,403 A | 5/1962 | Neefe | |
| RE25,286 E | 11/1962 | Decarle | |
| 3,210,894 A | 10/1965 | Bentley et al. | |
| 3,227,507 A | 1/1966 | Feinbloom | |
| 3,339,997 A | 9/1967 | Wesley | |
| 3,420,006 A | 1/1969 | Barnett | |
| 3,431,327 A | 3/1969 | Tsuetaki | |
| 3,482,906 A | 12/1969 | Volk | |
| 3,542,461 A | 11/1970 | Girard et al. | |
| 3,693,301 A | 9/1972 | Lemaltre | |
| 3,922,728 A | 12/1975 | Krasnov | |
| 3,932,148 A | 1/1976 | Krewalk, Sr. | |
| 4,055,378 A | 10/1977 | Feneberg et al. | |
| 4,062,629 A | 12/1977 | Winthrop | |
| 4,118,808 A * | 10/1978 | Poler ........................ 623/6.41 |
| 4,162,122 A | 7/1979 | Cohen | |
| 4,195,919 A | 4/1980 | Shelton | |
| 4,199,231 A | 4/1980 | Evans | |
| 4,210,391 A | 7/1980 | Cohen | |

(Continued)

FOREIGN PATENT DOCUMENTS

AU   3225789   10/1989

(Continued)

OTHER PUBLICATIONS

Menzo et al. J Cataract Refract. Surg Aug. 24, 1998.

(Continued)

*Primary Examiner*—David J Isabella
*Assistant Examiner*—Urmi Chattopadhyay
(74) *Attorney, Agent, or Firm*—Advanced Medical Optics, Inc.

(57) ABSTRACT

An intraocular lens (IOL) has been provided with an accommodation assembly that effects axial movement of the IOL optic through both the radial action of ciliary muscles and the axial forces resulting from vitreous pressure on the posterior wall of the capsular bag. In a preferred embodiment, the assembly comprises an IOL having substantially rigid, posteriorly extending fixation members which extend through slots in an accommodation ring encircling the optic. Axial forces exerted by vitreous fluids on the posterior wall of the capsular bag are transmitted from the posterior wall to the ring to the fixation members at the slot areas, causing axial movement of the IOL. At the same time, the angulation of the haptics converts radial forces due to contraction or expansion of the capsular bag into axial forces, causing still more axial movement of the IOL.

19 Claims, 1 Drawing Sheet

U.S. PATENT DOCUMENTS

| | | | |
|---|---|---|---|
| 4,240,719 | A | 12/1980 | Guilino et al. |
| 4,253,199 | A | 3/1981 | Banko |
| 4,254,509 | A | 3/1981 | Tennant |
| 4,274,717 | A | 6/1981 | Davenport |
| 4,307,945 | A | 12/1981 | Kitchen et al. |
| 4,315,673 | A | 2/1982 | Guilino et al. |
| 4,316,293 | A | 2/1982 | Bayers |
| 4,338,005 | A | 7/1982 | Cohen |
| 4,340,283 | A | 7/1982 | Cohen |
| 4,370,760 | A | 2/1983 | Kelman |
| 4,377,329 | A | 3/1983 | Poler |
| 4,402,579 | A | 9/1983 | Poler |
| 4,404,694 | A | 9/1983 | Kelman |
| 4,409,691 | A | 10/1983 | Levy |
| 4,418,991 | A | 12/1983 | Breger |
| 4,476,591 | A | 10/1984 | Arnott |
| 4,504,982 | A | 3/1985 | Burk |
| 4,551,864 | A | 11/1985 | Akhavi |
| 4,560,383 | A | 12/1985 | Leiske |
| 4,573,775 | A | 3/1986 | Bayshore |
| 4,580,882 | A | 4/1986 | Nuchman et al. |
| 4,596,578 | A | 6/1986 | Kelman |
| 4,618,228 | A | 10/1986 | Baron et al. |
| 4,618,229 | A | 10/1986 | Jacobstein et al. |
| 4,636,049 | A | 1/1987 | Blaker |
| 4,636,211 | A | 1/1987 | Nielsen et al. |
| 4,637,697 | A | 1/1987 | Freeman |
| 4,641,934 | A | 2/1987 | Freeman |
| 4,676,792 | A | 6/1987 | Praeger |
| 4,687,484 | A | 8/1987 | Kaplan |
| 4,693,572 | A | 9/1987 | Tsnetaki et al. |
| RE32,525 | E | 10/1987 | Pannu |
| 4,702,244 | A | 10/1987 | Mazzocco |
| 4,704,016 | A | 11/1987 | DeCarle |
| 4,720,286 | A | 1/1988 | Bailey et al. |
| 4,725,278 | A | 2/1988 | Shearing |
| 4,752,123 | A | 6/1988 | Blaker |
| 4,759,762 | A | 7/1988 | Grendahl |
| 4,769,033 | A | 9/1988 | Nordan |
| 4,790,847 | A | 12/1988 | Woods |
| 4,813,955 | A | 3/1989 | Achatz et al. |
| 4,830,481 | A | 5/1989 | Futhey et al. |
| 4,842,601 | A | 6/1989 | Smith |
| 4,881,804 | A | 11/1989 | Cohen |
| 4,888,012 | A | 12/1989 | Horn et al. |
| 4,888,015 | A | 12/1989 | Domino |
| 4,888,016 | A | 12/1989 | Langerman |
| 4,890,912 | A | 1/1990 | Visser |
| 4,890,913 | A | 1/1990 | DeCarle |
| 4,892,543 | A | 1/1990 | Turley |
| 4,898,461 | A | 2/1990 | Portney |
| 4,906,246 | A | 3/1990 | Grendahl |
| 4,917,681 | A | 4/1990 | Nordan |
| 4,919,663 | A | 4/1990 | Grendahl |
| 4,921,496 | A | 5/1990 | Grendahl |
| 4,923,296 | A | 5/1990 | Erickson |
| 4,932,966 | A | 6/1990 | Christie et al. |
| 4,932,968 | A | 6/1990 | Caldwell, Delmar R. et al. |
| 4,938,583 | A | 7/1990 | Miller |
| 4,955,902 | A | 9/1990 | Kelman |
| 4,976,534 | A | 12/1990 | Milge et al. |
| 4,976,732 | A | 12/1990 | Vorosmarthy |
| 4,990,159 | A | 2/1991 | Kraff |
| 4,994,082 | A | 2/1991 | Richards et al. |
| 5,000,559 | A | 3/1991 | Takahashi et al. |
| 5,002,382 | A | 3/1991 | Seidner |
| 5,019,098 | A | 5/1991 | Mercier |
| 5,019,099 | A | 5/1991 | Nordan |
| 5,047,052 | A | 9/1991 | Dubroff |
| 5,071,432 | A | 12/1991 | Baikoff |
| 5,089,024 | A | 2/1992 | Christie et al. |
| 5,096,285 | A | 3/1992 | Silberman |
| 5,112,351 | A | 5/1992 | Christie et al. |
| 5,147,397 | A | 9/1992 | Christ et al. |
| 5,158,572 | A | 10/1992 | Nielsen |
| 5,166,711 | A | 11/1992 | Portney |
| 5,166,712 | A | 11/1992 | Portney |
| 5,171,266 | A | 12/1992 | Wiley et al. |
| 5,173,723 | A | 12/1992 | Volk |
| 5,192,317 | A | 3/1993 | Kalb |
| 5,192,318 | A | 3/1993 | Schneider |
| 5,201,762 | A | 4/1993 | Hauber |
| 5,225,858 | A | 7/1993 | Portney |
| 5,258,025 | A | 11/1993 | Fedorov et al. |
| 5,260,727 | A | 11/1993 | Oksman et al. |
| 5,270,744 | A | 12/1993 | Portney |
| 5,275,623 | A | 1/1994 | Sarfarazi |
| 5,354,335 | A | 10/1994 | Lipshitz et al. |
| RE34,998 | E | 7/1995 | Langerman |
| 5,443,506 | A | 8/1995 | Garabet |
| 5,476,514 | A | 12/1995 | Cumming |
| 5,480,428 | A | 1/1996 | Fedorov et al. |
| 5,489,302 | A | 2/1996 | Skottun |
| 5,496,366 | A | 3/1996 | Cumming |
| 5,521,656 | A | 5/1996 | Portney |
| 5,562,731 | A | 10/1996 | Cumming |
| 5,578,081 | A | 11/1996 | McDonald |
| 5,593,436 | A | 1/1997 | Langerman |
| 5,607,472 | A | 3/1997 | Thompson |
| 5,628,795 | A | 5/1997 | Langerman |
| 5,628,796 | A | 5/1997 | Suzuki |
| 5,652,014 | A | 7/1997 | Galin et al. |
| 5,652,638 | A | 7/1997 | Roffman et al. |
| 5,657,108 | A | 8/1997 | Portney |
| 5,674,282 | A | 10/1997 | Cumming |
| 5,682,223 | A | 10/1997 | Menezes et al. |
| 5,684,560 | A | 11/1997 | Roffman et al. |
| 5,766,244 | A | 6/1998 | Binder |
| 5,769,890 | A | 6/1998 | McDonald |
| 5,776,191 | A | 7/1998 | Mazzocco |
| 5,814,103 | A | 9/1998 | Lipshitz et al. |
| 5,824,074 | A | 10/1998 | Koch |
| 5,843,188 | A | 12/1998 | McDonald |
| 5,847,802 | A | 12/1998 | Meneles et al. |
| 5,876,442 | A | 3/1999 | Lipshitz et al. |
| 6,013,101 | A | 1/2000 | Israel |
| 6,096,078 | A | 8/2000 | McDonald |
| 6,176,878 | B1 | 1/2001 | Gwon et al. |
| 6,217,612 | B1 | 4/2001 | Woods |
| 6,231,603 | B1 | 5/2001 | Lang et al. |
| 6,485,516 | B2 * | 11/2002 | Boehm ..................... 623/6.49 |
| 6,695,881 | B2 * | 2/2004 | Peng et al. ................ 623/6.34 |
| 6,761,737 | B2 * | 7/2004 | Zadno-Azizi et al. ...... 623/6.37 |
| 2002/0138140 | A1 * | 9/2002 | Hanna ...................... 623/6.37 |
| 2003/0114927 | A1 * | 6/2003 | Nagamoto ................ 623/6.37 |
| 2003/0135272 | A1 * | 7/2003 | Brady et al. .............. 623/6.37 |

FOREIGN PATENT DOCUMENTS

| | | |
|---|---|---|
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0507292 | 10/1992 |
| EP | 0566170 | 10/1993 |
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |

| | | |
|---|---|---|
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9416648 | 8/1994 |
| WO | 9503783 | 2/1995 |
| WO | 9615734 | 5/1996 |
| WO | 9625126 | 8/1996 |
| WO | 9743984 | 11/1997 |
| WO | 0134067 | 5/2001 |
| ZA | 888414 | 11/1988 |

OTHER PUBLICATIONS

Fechner et al. J Cataract Refract. Surg Jan. 24, 1998.
AMO Specs, Model AC-218, 1992.
Chiron Vision, Nuvita MA20, 1997.
Mandell, Contact Lens Practice, $4^{TH}$ ED.
Partial Program Re: ASCRS Symposium, Showing Video Tape Shown Between Apr. 10-14 1999.
Video Tape "New Elliptical Accom. IOL for Cataract Surgery" Shown at ASCRS Symposium on Apr. 10, 1999.
Thornton, Accommodation in Pseudophakia 25, P159.
U.S. Appl. No. 09/390,380 Filed Sep. 3, 1999.
U.S. Appl. No. 09/522,326 Filed Mar. 9, 2000.
U.S. Appl. No. 09/532,910 Filed Mar. 22, 2000.
U.S. Appl. No. 09/565,036 Filed May 3, 2000.
U.S. Appl. No. 09/631,223 Filed Aug. 2, 2000.
U.S. Appl. No. 09/657,325 Filed Sep. 7, 2000.
U.S. Appl. No. 09/656,661 Filed Sep. 7, 2000.
U.S. Appl. No. 09/657,251 Filed Sep. 7, 2000.
U.S. Appl. No. 09/721,072 Filed Nov. 22, 2000.
U.S. Appl. No. 09/795,929 Filed Feb. 28, 2001.
U.S. Appl. No. 09/822,040 Filed Mar. 30, 2001.

* cited by examiner

ACCOMMODATING INTRAOCULAR LENS ASSEMBLY WITH MULTI-FUNCTIONAL CAPSULAR BAG RING

FIELD OF THE INVENTION

This invention relates to intraocular lenses (IOLs). More particularly, the invention relates to intraocular lenses which provide accommodating movement in the eye.

The human visual system includes the eyes, the extraocular muscles which control eye position within the eye socket, the optic and other nerves that connect the eyes to the brain, and particular areas of the brain that are in neural communication with the eyes. Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape within the capsular bag, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber behind the lens. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of the IOL, e.g., to become more convex to focus on near objects, or by moving the IOL along its optical axis. Examples of this latter approach are disclosed in U.S. Pat. No. 6,176,878 to Gwon et al. and U.S. Pat. No. 6,406,494 to Laquette et al. The contents of both these patents are incorporated herein by reference.

In a healthy eye, accommodation is achieved through the actions of the ciliary muscles as well as through changes in the pressure exerted by vitreous fluids on the capsular bag. Prior art accommodating IOLs have typically attempted to take advantage of one of these two naturally occurring mechanisms. For instance, one class of accommodating IOL, exemplified by the patent to Gwon et al., takes advantage of changes in the pressure of the vitreous fluids by placing the optic of the IOL in direct contact with the posterior wall of the capsular bag. Thus, axial forces on the capsular bag are transmitted directly to the optic. Another class of accommodating IOLs, exemplified by the patent to Laquette et al., takes advantage of the actions of the ciliary muscles by circumscribing the optic with a flexible, posteriorly extending movement assembly that converts contraction and expansion of the capsular bag into axial movement of the optic.

Both the posteriorly positioned IOLs of the type disclosed by Gwon et al. and the anteriorly vaulted IOLs disclosed by Laquette et al. are satisfactory in most respects. However, because each relies on only one of the two available mechanisms for moving the IOL axially, neither achieves as much as accommodation as would be available if both mechanisms were used.

Accordingly, it would be advantageous to provide an IOL accommodation assembly that converts both the action of the ciliary muscles and the forces resulting from vitreous pressure on the posterior wall of the capsular bag into axial movement of the IOL optic.

SUMMARY OF THE INVENTION

An intraocular lens (IOL) has been provided with an accommodation assembly that effects axial movement of the IOL optic through both the radial action of ciliary muscles and the axial forces resulting from vitreous pressure on the posterior wall of the capsular bag. The accommodation assembly is configured to retard or prevent cellular growth across the optic of the IOL. In addition, the assembly comprises separate pieces, allowing each component to be formed of different materials, and the properties of each to be independently optimized. The assembly is relatively straightforward, can be produced using conventional IOL manufacturing procedures, and can be inserted in the eye of a patient using surgical techniques which are the same or similar to techniques used with conventional IOLs.

According to one aspect of the invention, the assembly comprises an IOL having substantially rigid, posteriorly extending fixation members, or haptics, which pass through slots formed in an accommodation ring surrounding the IOL. The IOL and the accommodation ring are substantially separate from and independent of one another, with contact between them occurring only at the walls of the slots. Axial forces exerted by vitreous fluids on the posterior wall of the capsular bag are thus transmitted from the posterior wall to the ring to the fixation members at the slot areas, causing axial movement of the IOL. At the same time, the angulation of the haptics converts radial forces due to contraction or expansion of the capsular bag into axial forces, causing still more axial movement of the IOL. Thus, an effective amount of accommodation is achieved.

One of the advantages of the present invention is that the accommodation assembly is arranged such that the IOL optic is always spaced from the walls of the capsular bag. Because there is no direct contact between the capsular bag and the IOL optic, the potential for cellular growth across the optic is minimized. In a preferred embodiment, this potential is reduced still further by providing the accommodation ring with sharp, preferably square, corners which have been shown to deter such growth. Thus, such problems as posterior capsule opacification (PCO) of the optic, which can interfere with vision, and fibrosis of the capsular bag, which can reduce the bag's ability to contract and expand, are decreased.

In addition, the accommodation ring is preferably provided with a plurality of circumferentially spaced, radially extending positioning members which maintain a distance between the body of the ring and equator of the capsular bag. Preferably, each of the positioning members makes minimal contact with the capsular equator so that contraction of the bag is not inhibited.

Each and every feature described herein, and each and every combination of two or more of such features, is included within the scope of the present invention provided that the features included in such a combination are not mutually inconsistent.

Additional aspects, features, and advantages of the present invention are set forth in the following description and claims, particularly when considered in conjunction with the accompanying drawings in which like parts bear like reference numbers.

DETAILED DESCRIPTION OF THE DRAWINGS

Figure 1:
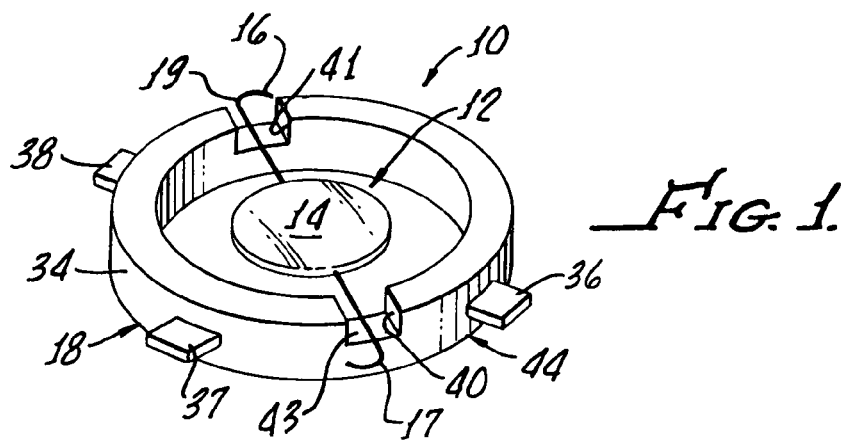
FIG. 1 is a perspective view showing an IOL accommodation assembly according to the present invention.

Referring to the drawings in more detail, an intraocular lens assembly 10 according to an exemplary embodiment of the present invention is illustrated in FIG. 1. The assembly 10 comprises an IOL 12, including an optic 14 and at least two fixation members 16, 17, and an accommodation ring 18. The optic 14 is adapted to focus light on a retina of an eye, while the fixation members 16, 17, are adapted to secure the optic within the capsular bag of the eye, and the accommodation ring 18 is adapted to transmit forces exerted by the ciliary muscles and vitreous fluids on the capsular bag to the fixation members 16, 17, as will be discussed in greater detail below.

The optic 14 of the IOL may be of any conventional shape or curvature depending on the type of vision correction needed. It may be constructed of rigid biocompatible materials, such as polymethyl methacrylate (PMMA), or flexible, deformable materials, such as silicone polymeric material, acrylic polymeric material, hydrogel polymeric material, and the like, which enable the lens body to be rolled or folded for insertion through a small incision in the eye.

The illustrated fixation members 16, 17 are filament-type haptics, although other types of relatively long and narrow fixation members, such as loop-type haptics, may also be used. The fixation members 16, 17 may be formed of any biocompatible material having sufficient rigidity to transmit forces from the capsular bag to the optic 14 yet flexible enough to minimize the risk of damage to the eye. Polymethyl methacrylate (PMMA) and polypropylene are two such materials, although other materials having similar characteristics will be readily apparent to one skilled in the art. In addition, the fixation members 16, 17 may be integral with or mechanically coupled to the optic 14, or secured thereto by adhesive or ultrasonic bonding. Regardless of the means of attachment used, the fixation members 16, 17 should be disposed at an angle such that the distal end 19 of each extends in a posterior direction relative to the optic 14.

Figure 2:
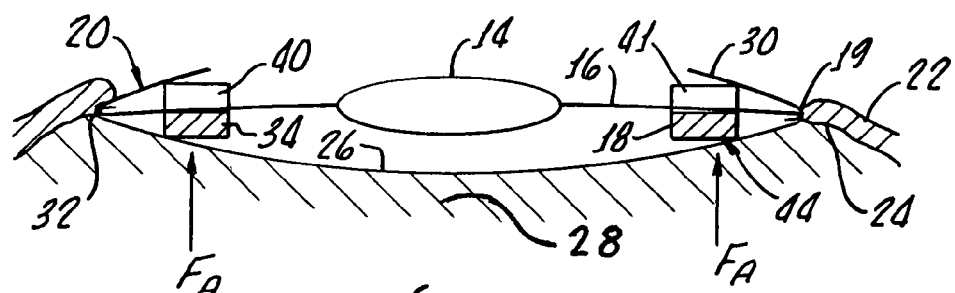
FIG. 2 is an cross-sectional elevation of the IOL accommodation assembly of FIG. 1 implanted in the posterior capsular of an eye.
Figure 3:
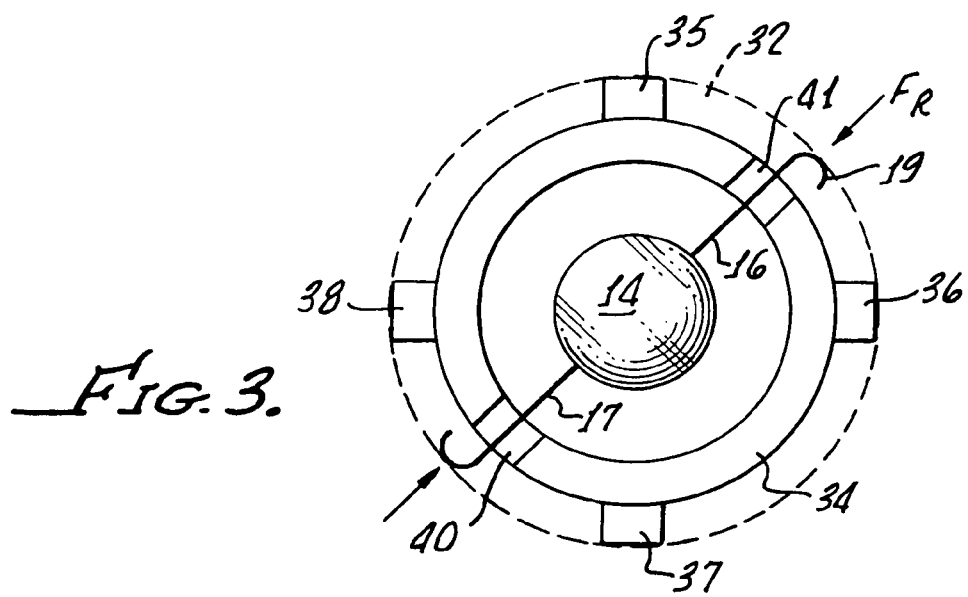
FIG. 3 is a plan view of FIG. 2.

The structure and function of the accommodation ring 18 may be best understood after reviewing the anatomy of the posterior chamber of the eye, the relevant portions of which are shown in FIG. 2. Briefly, the posterior chamber comprises the capsular bag 20, which is connected to a ciliary muscle 22 by suspensory ligaments or zonules 24. The capsular bag 20 includes a posterior wall 26 that separates the posterior chamber from the vitreous chamber 28, an anterior wall 30, which after removal of the natural crystalline lens is often called the anterior flap, and an equator 32 formed at the intersection between the posterior and anterior walls 26, 30.

In a healthy eye, the ciliary muscle 22 constricts for near vision, causing the capsular equator 32 to contract to its minimum diameter and the pressure of fluids in the vitreous chamber 28 to increase. Conversely, for far vision, the ciliary muscle 22 relaxes, causing the capsular equator 32 to expand to its maximum diameter and the vitreous chamber pressure to decrease. The accommodation ring 18 of the present invention is configured to take advantage of this natural behavior of the ciliary muscle by transmitting the axial and radial forces $F_A$ and $F_R$ from the vitreous chamber 28 and the capsular equator 32, respectively, to the fixation members 16, 17 and converting these forces into axial movement of the IOL optic 14.

The accommodation ring 18 comprises a ring body 34 having an outer diameter that is less than the diameter of the capsular equator 32 in its most contracted state. A plurality of circumferentially spaced positioning members 35, 36, 37, 38 extend radially outwardly from the outer surface of the ring body 34. The length of each positioning member 35, 36, 37, 38 is selected such that the distance from the outermost edge of one positioning member 35 to the outermost edge of a diametrically opposed positioning member 37 is approximately equal to the diameter of the capsular equator 32 in its most expanded state. Thus, the positioning members 35, 36, 37, 38 serve to maintain space between the ring body 34 and the capsular equator 32.

Each of the positioning members 35, 36, 37 and 38 has a width in the circumferential direction which is very small relative to the total circumference of the ring body 34. This results in minimal contact between the accommodation ring 18 and the capsular equator 32, and thus does not significantly interfere with contraction of the capsular bag 20.

The ring body 34 includes a plurality of slots 40, 41, each one receiving a different one of the fixation members 16, 17. Each slot 40, 41 has a posterior wall 43 extending transversely to its respective fixation member 16, 17 so that any forces $F_A$ exerted on the ring body 34 due to vitreous pressure are transmitted from the slot walls 43 to the fixation members 16, 17, causing the IOL optic 14 to move forward. These forces are added to the radial forces $F_R$ exerted on the fixation members 16, 17 by the ciliary muscles 22, thus resulting in greater accommodation than would be possible if only forces due to vitreous pressure were utilized.

The potential for epithelial cell growth across the optic 14 of the IOL 12 is relatively small, since the optic 14 does not directly contact the capsular bag 20. This potential may be reduced still further, however, by providing the ring body 34 with sharp, preferably square, corners 44, which have been shown to inhibit epithelial cell growth.

The accommodation ring 18 is preferably formed of a biocompatible material that is sufficiently deformable to allow it to be rolled, folded or otherwise compressed to facilitate its passage through a small incision in the eye. Because it is formed entirely separately from the IOL 12, however, it may be made of different material than the IOL optic 14 and fixation members 16, 17, and thus can have such properties as strength, hardness and rigidity optimized independently of the other elements.

The IOL 12 may be inserted into the capsular bag 20 of a mammalian eye using a two step procedure after the natural lens has been removed using a phacoemulsification technique. First, the accommodation ring 18 may be rolled or folded and inserted through a small incision, for example on the order of about 3.2 mm. Then the IOL 12 may also be rolled or folded and inserted through the same incision using any suitable insertion apparatus. After the IOL 12 has been inserted through the incision, the fixation members 16, 17 may be positioned in the slots 40, 41 of the ring body 34 and the distal ends of the fixation members 16, 17 tucked under the anterior flap 30 of the capsular bag 20 using the tip of the insertion apparatus or another tool favored by the ophthalmic surgeon.

If the IOL accommodation assembly 10 is to be implanted in an adult human eye, the optic 14 preferably has a diameter in the range of about 3.5 mm to about 7 mm and, more preferably, in the range of about 5 mm to 6 mm. Further, the accommodation assembly 10 may have an overall diameter, with fixation members 16, 17 and accommodation ring 18 in unstressed conditions, of about 8 mm to about 13 mm. Additionally, the optic 14 preferably has a far vision correction power for infinity in an unaccommodated state.

While the present invention has been described with respect to various specific examples and embodiments, it is to be understood that the invention is not limited thereto and that it can be variously practiced within the scope of the following claims.

What is claimed is:

1. An intraocular lens assembly comprising:
   an optic adapted to focus light to a retina of an eye and having a central optical axis; and
   accommodation means for positioning the optic in the capsular bag of an eye, the capsular bag including an equator, a posterior wall and an anterior flap, the accommodation means including
   first means encircling the optic for transmitting axial forces and radial forces to a second means for maintaining the optic in forwardly spaced relationship to the posterior wall of the capsular bag, causing axial movement of the optic;
   the second means extending outside and beyond an outer perimeter of the first means.

2. The assembly of claim 1, wherein the second means comprises a plurality of fixation members extending radially from the optic, each of the fixation members having a proximal end coupled to the optic and a distal end configured for placement in the equator of the capsular bag, the distal end extending posteriorly of the optic when the assembly is implanted in an eye.

3. The assembly of claim 2, wherein the fixation members comprise at least two filament-type haptics.

4. The assembly of claim 2, wherein the first means comprises a slotted element encircling the optic, the fixation members extending through the element such that axial forces exerted on the element by the posterior wall are transmitted to the fixation members.

5. The intraocular lens assembly according to claim 2, wherein each of the fixation members is formed of sufficiently rigid material to translate compressive forces exerted by the ciliary muscle on the equator of the capsular bag into anterior movement of the optic.

6. The intraocular lens assembly according to claim 4, wherein the slotted element comprises a substantially circular ring body.

7. The intraocular lens assembly according to claim 4, wherein the slotted element comprises:
   a ring body; and
   a plurality of circumferentially spaced positioning members extending outwardly from the ring body for maintaining a distance between the ring body and the equator of the capsular bag.

8. The intraocular lens assembly according to claim 7, wherein the ring body has a predetermined circumference, and wherein each of the positioning members has a sufficiently small width relative to the circumference of the ring body to minimally inhibit contraction of the capsular bag.

9. The intraocular lens assembly according to claim 4, wherein the slotted element is formed from a first material and the fixation members are formed from a second material having different properties from the first material.

10. The intraocular lens assembly according to claim 4, wherein the slotted element includes an edge surface extending between a posterior surface and an anterior surface, the edge surface intersecting with a least one of the posterior surface and the anterior surface to form a sharp edge corner therewith.

11. An intraocular lens assembly for insertion into an eye having a capsular bag controlled by a ciliary muscle, the capsular bag including an equator, a posterior wall, and an anterior flap, the assembly including:
   an intraocular lens comprising an optic having an optic axis and a plurality of fixation members extending radially from the optic; and
   an accommodation ring configured to extend around the optic in radially spaced relationship thereto, the accommodation ring having a posterior surface for placement against the posterior wall of the capsular bag, an anterior surface for placement against the anterior flap of the capsular bag, and an outer perimeter, each of the fixation members extending outside and beyond the outer perimeter.

12. The intraocular lens assembly according to claim 11, wherein each of the fixation members has a proximal end coupled to the optic and a distal end for placement in the equator of the capsular bag, the distal end extending posteriorly to the proximal end when the assembly is inserted in the eye.

13. The intraocular lens assembly according to claim 12, wherein each of the fixation members is formed of sufficiently rigid material to translate compressive forces exerted by the ciliary muscle on the equator of the capsular bag into anterior movement of the optic.

14. The intraocular lens assembly according to claim 11, wherein the accommodation ring comprises a substantially circular ring body.

15. The intraocular lens assembly according to claim 11, wherein the accommodation ring comprises:
   a ring body; and
   a plurality of circumferentially spaced positioning members extending outwardly from the ring body for maintaining a distance between the ring body and the equator of the capsular bag.

16. The intraocular lens assembly according to claim 15, wherein the ring body has a predetermined circumference, and wherein each of the positioning members has a sufficiently small width relative to the circumference of the ring body to minimally inhibit contraction of the capsular bag.

17. The intraocular lens assembly according to claim 15, further comprising a plurality of radially extending slots, each of the slots being located in the ring body at a location circumferentially spaced from the positioning members.

18. The intraocular lens assembly according to claim 11, wherein the accommodation ring is formed from a first material and the fixation members of the intraocular lens are formed from a second material having substantially different properties from the first material.

19. The intraocular lens assembly according to claim 11, wherein the accommodation ring includes an edge surface extending between the posterior surface and the anterior surface, the edge surface intersecting with a least one of the posterior surface and the anterior surface to form a sharp edge corner therewith.

* * * * *